United States Patent [19]

Jonckers et al.

[11] Patent Number: 4,866,207

[45] Date of Patent: Sep. 12, 1989

[54] PROCESS FOR CONCENTRATING AN UREA SOLUTION BY EVAPORATION

[75] Inventors: Kees Jonckers, Roosteren; Henk C. Burks, Oirsbeek, both of Netherlands

[73] Assignee: Stamicarbon B.V., Geleen, Netherlands

[21] Appl. No.: 6,185

[22] Filed: Jan. 23, 1987

[51] Int. Cl.$^4$ ............... C07C 126/02; C07C 126/08
[52] U.S. Cl. ........................... 564/73; 564/70; 564/71
[58] Field of Search ............... 564/71, 70, 73

[56] References Cited

U.S. PATENT DOCUMENTS

| | | | |
|---|---|---|---|
| 3,137,725 | 6/1984 | Cook et al. | 564/71 X |
| 3,446,601 | 5/1969 | Heunks et al. | 564/71 X |
| 4,231,951 | 11/1980 | Konoki et al. | 564/65 |
| 4,341,640 | 7/1982 | Landis | 564/73 X |
| 4,354,040 | 10/1982 | Inoue et al. | 564/67 |
| 4,613,696 | 9/1986 | Zardi | 564/73 X |
| 4,747,915 | 5/1988 | Pagani | 564/73 X |

FOREIGN PATENT DOCUMENTS

| | | | |
|---|---|---|---|
| 0145054 | 6/1985 | European Pat. Off. | 534/65 |
| 61-10547 | 1/1986 | Japan | 564/71 |
| 144842 | 4/1962 | U.S.S.R. | 564/71 |
| 1110280 | 4/1968 | United Kingdom | 564/71 |
| 2040283 | 8/1980 | United Kingdom | 534/65 |
| 2058764 | 4/1981 | United Kingdom | 564/73 |

*Primary Examiner*—Floyd D. Higel
*Attorney, Agent, or Firm*—Cushman, Darby & Cushman

[57] ABSTRACT

An improved process and apparatus for the concentration of an aqueous urea solution by evaporation of water in a single pass shell and tube heat exchanger having a substantially vertical tube bundle within the shell. The aqueous urea solution is introduced into the top of the vertical tube bundle and caused to fall as a film down the inside of said tubes whereby it is heated and water evaporated therefrom to form a concentrated urea solution. The heat for this evaporation is provided by condensing at least a part of a gas mixture containing $NH_3$, $CO_2$ and $H_2O$ in the shell side of the heat exchanger. This gas mixture is introduced into a lower portion of the shell wherein it is caused to flow upwardly in shell in contact with said tube bundle, counter-current to the flow of the aqueous urea solution within the tubes whereby heat from said condensation is transferred to said aqueous urea solution flowing down the inside of the tubes. The shell side is provided with baffle means adapted to permit the gas mixture and condensate to flow upwardly in the shell side in contact with the tubes, while substantially preventing the back flow of either the gas mixture or the condensate within the shell side.

4 Claims, 1 Drawing Sheet

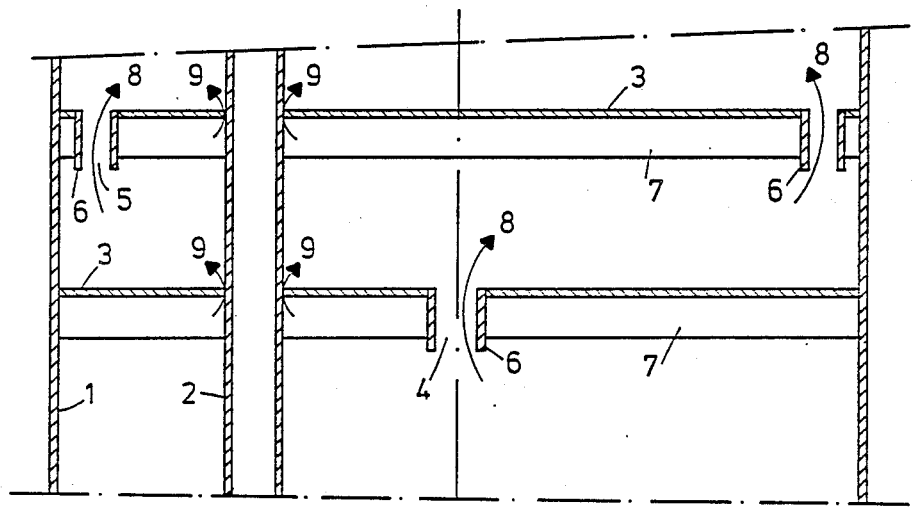

PROCESS FOR CONCENTRATING AN UREA SOLUTION BY EVAPORATION

The invention relates to a process for concentrating a urea solution by evaporation of water from the urea solution. The invention also relates to an installation for carrying out this process.

In the preparation of urea from carbon dioxide and an excess of ammonia a urea synthesis solution containing carbamate and free ammonia is first formed in the synthesis zone. The carbamate is decomposed into ammonia and carbon dioxide and the decomposition products are removed from the solution in a number of steps, together with part of the ammonia and water present in the solution. A urea solution in water is ultimately obtained which contains approximately 70–75% by weight of urea and in which ammonia and carbon dioxide are still present. This solution is not suitable for fertilization purposes or application in the manufacture of resins. As a rule, it must first be processed to form solid urea. In this process the approximately 25–30% by weight of water and the ammonia and carbon dioxide still present are removed by evaporation, or the urea in the solution is allowed to crystallize and the crystals are melted, upon which the resulting urea melt is converted into granules. Since exposing urea solutions to high temperatures results in the decomposition of urea and the formation of biuret, which biuret is undesirable in the application of urea for fertilization purposes as well as for resin manufacture, urea solutions are usually evaporated under reduced pressure to avoid excessively high evaporation temperatures. In addition to this, for economic reasons the evaporation process is mostly carried out in two or more steps, in which most of the water present is removed at a moderately reduced pressure in the first step(s), upon which the evaporation is continued under a much lower pressure in the last step until a urea melt is obtained that is practically free from water, containing less than 0.5% by weight of water.

In practice, so-called vertical-one-pass evaporators are mostly used for this process, in which the solution and the obtained vapour are fed upwards through the tubes of a vertical bundle of tubes, the heat required for the evaporation being supplied by condensation of low-pressure steam in the shell space provided around the tube bundle.

It has already been suggested to utilize the heat that can be generated from gaseous and liquid process flows obtained during the urea synthesis for concentrating urea solutions in the first evaporation step, see, for example, EP-A-No. 145.054. The procedure described in this patent application concerns a urea synthesis in which, at a pressure between 125 and 350 bar, a urea synthesis solution which, besides urea and water, still contains carbamate and free ammonia is first formed in a synthesis zone, upon which this urea synthesis solution is processed in three decomposition steps, at synthesis pressure in the first step, at a pressure of 4–40 bar in the second step and 1–10 bar in the third decomposition step, to decompose carbamate and to remove from the solution the decomposition products together with the free ammonia present in the solution as well as an amount of water, and the remaining solution is finally concentrated in two evaporation steps. The heat required in the first evaporation step is obtained by condensation of the gas mixture obtained at a pressure of 4–40 bar in the second decomposition step. If the dew point of the gas mixture is increased, for instance by adding the aqueous carbamate solution formed in the third decomposition step to the condensing gas mixture, so that the condensation commences at a higher temperature, the released absorption and condensation heat is obtained at such a temperature level that, if the heat exchange is carried out countercurrently, a urea solution with a concentration of, for example, approx. 95% by weight and a temperature of, for example, approx. 130° C., depending on the pressure applied in the tubes of the evaporator, can be discharged from the first evaporator step. However, if this procedure is to be carried out in a vertical-one-pass evaporator, in which the urea solution to be concentrated is fed upwards through the tubes of the evaporator and the gas mixture to be condensed and the aqueous carbamate solution are fed downwards through the shell, there is a real risk of insufficient wetting and insufficiently uniform distribution of the gas mixture over the outside of the tubes in the shell space, as a result of which a uniform transfer of heat to the urea solution to be concentrated cannot be ensured.

The aim of the invention is to provide a procedure for the evaporation of a urea solution and an installation for applying the process, in which use is made of the heat that can be generated from process flows as described in EP-A-No. 145.054, in which the above disadvantages are avoided. This aim is achieved according to the invention when the gas mixture to be condensed is passed countercurrently to the urea solution to be concentrated upwards through the heating area, which heating area is designed as a submerged condenser in which the flow profile of the gas mixture and the condensate formed more or less corresponds to the flow profile of a so-called plug flow, in which no back-mixing of the ongoing flow with the reagents in the heating zone occurs.

The invention therefore relates to a process for concentrating a urea solution by evaporation of water therefrom, in which process the urea solution is passed as a film along the inside of the tubes of a vertical bundle of tubes and the heat required for the evaporation of water is generated substantially by condensation of a gas mixture containing $NH_3$, $CO_2$ and $H_2O$ in a heating area provided around the bundle of tubes, in which the gas mixture containing $NH_3$, $CO_2$ and $H_2O$ is supplied to the heating area near one end of the tubes of the tube bundle and the urea solution is supplied to the other end of the tube bundle. The process is characterized in that the gas mixture containing $NH_3$, $CO_2$ and $H_2O$ is fed substantially upwards through the heating area and it is ensured that the gas mixture or condensate cannot flow back.

It is advantageous to add an aqueous carbamate solution to the gas mixture containing $NH_3$, $CO_2$ and $H_2O$ in the heating area, since this increases the dew point of the gas mixture, as a result of which condensation commences at a higher temperature level. The aqueous carbamate solution is preferably supplied to the heating area at a point situated between the supply of urea solution to the tubes of the tube bundle and the supply of the gas mixture containing $NH_3$, $CO_2$ and $H_2O$ to the heating zone.

Backmixing of the reaction mixture can be prevented by applying a number of perforated horizontal baffles in the heating area to divide the latter into compartments situated one above the other, while choosing the feed rate of the gas mixture containing $NH_3$, $CO_2$ and $H_2O$ relative to the flow area to be such that a gas cushion is formed at the top of each compartment, from which the gas flows through the apertures into the above compartments where it will exert such a pressure on the liquid present near the apertures that the liquid is prevented from flowing back through the apertures. The presence of the gas cushion makes it possible, when special measures are taken, to pass the gas mixture containing $NH_3$, $CO_2$ and $H_2O$ and the condensate separately, through different apertures in the baffles, to the compartments above.

The invention also provides an installation for applying the above process. This installation consists of a vertical bundle of tubes surrounded by a heating area and is provided with means to allow the urea solution to flow as a film in downward direction along the inside of the tubes of the tube bundle. The installation is characterized in that the heating area is divided, by means of perforated horizontal baffles, into compartments situated one above the other and in that there are supply and discharge lines to pass the gas mixture containing $NH_3$, $CO_2$ and $H_2O$ and the condensate substantially upwards through the compartments.

The number and location of the apertures in the baffles at least corresponds to the number and location of the tubes in the tube bundle. If the number and the locations of the apertures in the baffles correspond to the number and the location of the tubes in the bundle of tubes, the reagents will flow from one compartment into the next-higher compartment exclusively through the gaps remaining upon installation of the tubes of the tube bundle through the apertures in the baffles as a result of the tolerance of the apertures. As a rule, a larger flow area will be required between the compartments if the flow through the heating area required for an efficient heat exchange with the urea solution to be evaporated is to be realized. In that case the baffles are to be provided with additional apertures. By providing at least part of these additional apertures with a rim projecting downwards, the possibility of maintaining a gas cushion in the compartments will be simplified, since the apertures provided with a rim will then not function as flow area for the gas phase. Applying rims around the apertures also provides the possibility of realizing separate flows, through different apertures, of the liquid and gas phases to the compartments above, which considerably reduces the risk of the two phases flowing back.

According to a preferred embodiment, the baffles are provided with a first group of apertures through which at least the tubes of the tube bundle extend and a second group of apertures which are applied alternately in the centre and near the circumference of the baffle. If only the apertures of the second group are provided with a rim projecting downwards, the gas mixture containing $NH_3$, $CO_2$ and $H_2O$ will flow into the higher compartments at least substantially through the gaps around the tubes of the tube bundle. The condensate will flow alternately through the apertures in the centre and those near the circumference. Such a design will ensure that the separate compartments function as bubble-type scrubbers in which adequate contact is realized between the gas phase and the liquid phase, while the flow of the reagents, regarded over the entire heating zone, shows all the characteristics of plug flow. The adequate contact in the compartments between the gas phase and the liquid phase and the cooling effect of the relatively cold urea solution in the tubes of the tube bundle results in a rapid absorption and condensation in the compartments of part of the gas mixture containing $NH_3$, $CO_2$ and $H_2O$. The heat released in this process is transferred via the tube walls to the urea solution to be evaporated, which flows down along the inside of the tubes.

The process according to the invention can be suitably applied to urea processes involving a decomposition step in the pressure range of 4–40 bar, since the absorption and condensation heat obtained in condensation, with the help of a carbamate solution, in the mentioned pressure range of the gas mixture obtained in this decomposition step as a rule has such a temperature level that a urea solution of approximately 70% by weight can be concentrated to approximately 95% by weight.

It is obviously possible to design the bottom part of the heating area as a steam jacket. This will be done preferably if the gas mixture resulting from the decomposition step operated at 4–40 bar becomes available at a relatively low pressure, for example 4–12 bar, or if the urea solution from the first evaporation step is required to be carried off at a temperature of at least 130° C.

The invention will be elucidated with the help of the figure and the following example without, however, being limited hereto.

The figure gives a schematic cross section of part of the heating area showing two baffles and one tube of the tube bundle.

The outer shell of the heating area is indicated by 1, a tube of the tube bundle by 2, the baffles by 3, the central aperture by 4, the apertures near the circumference by 5, the rims projecting downwards by 6 and the gas cushions by 7. The liquid phase flows in the direction indicated by arrows 8 and the gas phase flows in the direction indicated by arrows 9.

The urea solution to be concentrated is supplied as a film running down the the inside of the tubes 2.

EXAMPLE

Urea is prepared according to the embodiment as schematically represented in the figure in EP-A-No. 145.054, with the understanding that the first evaporation step indicated in this figure by number 12 is designed and operated in the manner described in the present invention. The heating area around the tubes is divided into ten compartments by means of baffles. The baffles have apertures applied alternately in the centre and near the circumference which are provided with a rim projecting downwards and through which an upward flow of the liquid phase through the compartments is realized. The gas mixture containing $NH_3$, $CO_2$ and $H_2O$ flows to the successive, higher compartments via the gaps between the tubes and the baffles. In addition, extra apertures for the gas flow have been applied, in decreasing numbers, between the tubes in the successive baffles.

The following data relate to an installation with a capacity of 1500 tonnes per day. The amounts are indicated in kg per hour.

35,414 kg of $NH_3$ and 45,863 kg of $CO_2$ are fed to the high pressure part of the installation. The pressure in this high pressure part, comprising a synthesis zone, a first decomposition step, a condensation zone and a scrubbing zone for the inert gases, amounts to 140 bar. The pressure in a second decomposition step and in the heating area of the first evaporation step amounts to 17.7 bar. The pressure in a third decomposition step is 3.9 bar. A gas mixture from the second decomposition step, containing 14,139 kg of $CO_2$, 8,711 kg of $NH_3$ and 3,301 kg of $H_2O$, is supplied to the bottom compartment of the heating zone surrounding the bundle of tubes. The temperature of this gas mixture is 158.6° C., its dew point being 143.4° C. By subjecting this mixture to heat exchange with 86,623 kg of the urea solution flowing down the tubes as a film, which is supplied at a temperature of 95° C. and contains 63,525 kg of urea, 210 kg of biuret, 28 kg of $CO_2$, 377 kg of $NH_3$ and for the rest water, this gas mixture is cooled and condensed. The condensation and absorption of the gas mixture is continued with the help of 20,944 kg of carbamate solution resulting from the third decomposition step, containing 4,294 kg of $CO_2$, 7400 kg of $NH_3$, 9,229 kg of $H_2O$ and 21 kg of urea, which is supplied to the third compartment of the heating area at a temperature of 47° C. 47,079 kg of a carbamate solution with a temperature of 93.7° C. and containing 18,427 kg of $CO_2$, 16,102 kg of $NH_3$, 12,529 kg of $H_2O$ and 21 kg of urea is discharged from the top compartment of the heating area. In addition, 45 kg of a gas mixture still containing 6.3 kg of $CO_2$, 9.1 kg of $NH_3$, 0.8 kg of $H_2O$ and for the rest inert gas is discharged from this compartment.

An amount of 67,833 kg of concentrated urea solution with a temperature of 122.5° C. is carried off from the bottom part of the bundle of tubes. This solution contains 63,144 kg of urea, 264 kg of biuret, 0.02 kg of $CO_2$, 4.7 kg of $NH_3$ and 4420 kg of $H_2O$.

We claim:

1. In a process for the concentration of an aqueous urea solution by evaporation of water therefrom in a single pass shell and tube heat exchanger having a substantially vertical tube bundle within said shell, wherein the aqueous urea solution to be concentrated is fed into the tubes of said tube bundle, and the heat required for said evaporation of water is substantially generated by condensation of a gas mixture containing $NH_3$, $CO_2$ and $H_2O$ in the shell side of said heat exchanger surrounding said tube bundle, the improvement essentially comprising:

introducing said aqueous urea solution to be concentrated into the top of said vertical tube bundle wherein it is caused to fall as a film down the inside of said tubes whereby said aqueous urea solution is heated and water evaporated therefrom, thereby forming a concentrated urea solution which is removed from the bottom of said tube bundle;

introducing said gas mixture containing $NH_3$, $CO_2$ and $H_2O$ into a lower portion of the shell side of said heat exchanger wherein it is caused to flow upwardly in said shell side in contact with said tube bundle, counter-current to the flow of said aqueous urea solution within said tubes;

condensing at least a part of said gas mixture in said shell side to form a condensate which is removed from a top portion of said shell, whereby heat from said condensation is transferred to said aqueous urea solution flowing down the inside of said tubes; and carrying out such condensation within the shell side of said heat exchanger in a plurality of compartments separated by means of baffles adapted to permit said gas mixture and condensate to flow upwardly between adjacent compartments in said shell side in contact with said tubes, while substantially preventing the back flow of either said gas mixture or condensate downwardly between adjacent compartments within said shell side.

2. The process of claim 1 wherein an aqueous ammonium carbamate solution is introduced into the gas mixture in the shell side of said vertical heat exchanger at a point above the point of introduction of said gas mixture into said shell side, and below the point of introduction of said aqueous urea solution into said tube bundle.

3. The process of claim 1 or 2 wherein said shell side surrounding said tube bundle is divided into a number of compartments situated one above the other by means of horizontal baffles having apertures interconnecting said compartments, the flow area of said apertues and the feed rate of gas mixture into said shell side being chosen such that a gas cushion is formed at the top of each compartment beneath a baffle, whereby the back flow of either said gas mixture or condensate within said shell side is substantially prevented.

4. The process of claim 3 wherein the configuration of said baffles is such that the flow of said gas mixture from a lower to a higher compartment in said shell side is through different apertures than the flow of condensate from said lower to said higher compartment.

* * * * *

UNITED STATES PATENT AND TRADEMARK OFFICE
CERTIFICATE OF CORRECTION

PATENT NO. : 4,866,207
DATED : September 12, 1989
INVENTOR(S) : Kees JONCKERS and Henk C. BURKS It is certified that error appears in the above-identified patent and that said Letters Patent is hereby corrected as shown below:

In the front page of the patent, please insert foreign application priority information as follows:

-- [30]    Foreign Application Priority Data

Nov. 3, 1986   [NL]   Netherlands .......... 8602769 --.

Signed and Sealed this

Twentieth Day of November, 1990

Attest:

HARRY F. MANBECK, JR.

*Attesting Officer*      *Commissioner of Patents and Trademarks*